United States Patent
Wu

(10) Patent No.: US 12,376,751 B2
(45) Date of Patent: Aug. 5, 2025

(54) SYSTEMS AND METHODS FOR LIVING THING PRESENCE DETECTION USING A RADAR SYSTEM

(71) Applicant: Airtouch (Shanghai) Intelligent Technology Co., Ltd, Shanghai (CN)

(72) Inventor: Huaping Wu, Shanghai (CN)

(73) Assignee: Airtouch (Shanghai) Intelligent Technology Co., Ltd, Shanghai (CN)

( * ) Notice: Subject to any disclaimer, the term of this patent is extended or adjusted under 35 U.S.C. 154(b) by 252 days.

(21) Appl. No.: 17/878,076

(22) Filed: Aug. 1, 2022

(65) Prior Publication Data

US 2023/0043652 A1    Feb. 9, 2023

(30) Foreign Application Priority Data

Aug. 3, 2021    (CN) .......................... 202110885917.4

(51) Int. Cl.
*A61B 5/0205*    (2006.01)
*G01S 13/56*     (2006.01)
*G01S 13/88*     (2006.01)

(52) U.S. Cl.
CPC ............ *A61B 5/0205* (2013.01); *G01S 13/56* (2013.01); *G01S 13/88* (2013.01)

(58) Field of Classification Search
None
See application file for complete search history.

(56) References Cited

U.S. PATENT DOCUMENTS

| | | | | |
|---|---|---|---|---|
| 5,448,501 A | * | 9/1995 | Hablov | A61B 5/0507 342/28 |
| 2020/0124706 A1 | * | 4/2020 | Buddendick | G01S 13/343 |
| 2021/0247483 A1 | * | 8/2021 | Wang | G01S 13/003 |

* cited by examiner

*Primary Examiner* — Bernarr E Gregory
(74) *Attorney, Agent, or Firm* — IPRTOP LLC

(57) ABSTRACT

Embodiments of the disclosure include a Radar system for detecting presence of a living thing. The radar system includes a transmitter/receiver module configured to emit radio signals to an environment surrounding the Radar system and to detect returned radio signals from the environment, and a large-movement detection sub-module configured to determine a large movement of the living thing based on the returned radio signals. The radar system also includes a micro-movement detection sub-module configured to determine a micro movement of the living thing based on the returned radio signals, and a breath and heartbeat detection sub-module configured to determine a breath or heartbeat of the living thing based on the returned radio signals. The radar system further includes a presence detection sub-module configured to determine the presence of the living thing based on determinations received from the corresponding detection sub-modules.

20 Claims, 7 Drawing Sheets

SYSTEMS AND METHODS FOR LIVING THING PRESENCE DETECTION USING A RADAR SYSTEM

CROSS-REFERENCE TO RELATED APPLICATION

This application claims the benefit of priority to Chinese Patent Application 2021108859174 filed Aug. 3, 2021, which is incorporated herein by reference in its entirety.

TECHNICAL FIELD

The present disclosure relates to systems and methods for detecting the presence of a living thing, and more particularly to, detecting presence of a living thing using a Radio Detection and Ranging (Radar) system implementing improved detection methods.

BACKGROUND

Radio detection systems such as Radio Detection and Ranging (Radar) systems have been widely used in advanced detection technologies, such as to detect the existence/presence of the objects/living beings and/or determine the properties of the same. For example, a typical Radar system measures the property (e.g., velocity, location, micro movement, etc.) of a target by reflecting off the target with electromagnetic waves (e.g., pulsed or continuous radio signals) and measuring the returned electromagnetic waves with a receiving antenna. Differences in the returned electromagnetic wave's return times, wavelengths, frequencies, and/or phases can then be used to determine the properties of the target. Because radio signals (e.g., long wavelength electromagnetic waves) can penetrate different mediums (e.g., clouds, fogs, mist, etc.), target multiple objects simultaneously, and can have high sensitivity at low cost, a Radar system is particularly suitable for applications such as detecting vehicles (e.g., sensing parking spaces), security (e.g., detecting the presence of an intruder), lighting, or for more delicate tasks such as monitoring human activities/micro movements in aiding home automations.

Specifically, when performing the living thing presence detection (e.g., in security systems for detecting an intruder or in home automation applications), existing methods mostly focus on detecting the breath of the living thing (e.g., a human being) by analyzing/processing the emitted and returned radio signals. They all suffer from various problems. For example, for those based on hardware filtering methods, the costs for design and manufacturing the infrastructures are high and the adaptability of the systems are low because of the hardware. Also, for those based on applying Fast Fourier transform (FFT) analysis on the entire bandwidth of the returned radio signals, the methods are generally time and computational resources consuming, and are inaccurate because of the noise in the returned radio signals.

Embodiments of the disclosure address the above problems by detecting living things presence using a Radar system implementing an improved detection method.

SUMMARY

In one example, embodiments of the disclosure include a Radio Detection and Ranging (Radar) system for detecting presence of a living thing. The radar system includes a transmitter/receiver module configured to emit radio signals to an environment surrounding the Radar system and to detect returned radio signals from the environment, and a large-movement detection sub-module configured to determine a large movement of the living thing based on the returned radio signals. The radar system also includes a micro-movement detection sub-module configured to determine a micro movement of the living thing based on the returned radio signals, and a breath and heartbeat detection sub-module configured to determine a breath or heartbeat of the living thing based on the returned radio signals. The radar system further includes a presence detection sub-module configured to receive determinations from the large-movement detection sub-module, the micro-movement detection sub-module, and the breath and heartbeat detection sub-module respectively, and to determine the presence of the living thing based on based on the received determinations.

In another example, embodiments of the disclosure include a method for detecting presence of a living thing implemented by a Radio Detection and Ranging (Radar) system. The method includes emitting, by a transmitter/receiver module, radio signals to an environment surrounding the Radar system and detecting, by the transmitter/receiver module, returned radio signals from the environment. The method also includes determining, by a large-movement detection sub-module, a large movement of the living thing based on the returned radio signals and determining, by a micro-movement detection sub-module, a micro movement of the living thing based on the returned radio signals. The method further includes determining, by a breath and heartbeat detection sub-module, a breath or heartbeat of the living thing based on the returned radio signals and determining, a presence determination sub-module, the presence of the living thing based on the determination of at least one of the large movement, the micro movement, and the breath or heartbeat determined by the corresponding determination module.

In a further example, embodiments of the disclosure include a non-transitory computer-readable medium encoded with instructions that, when executed by at least one processor of an apparatus, perform a process. The process includes emitting, by a transmitter/receiver module, radio signals to an environment surrounding the Radar system and detecting, by the transmitter/receiver module, returned radio signals from the environment. The process also includes filtering, by a first pre-process module, the returned radio signals using a first low-pass filter and generating, by the first pre-process module, a first pre-processed result by down sampling the returned radio signals using a first digital down-converter. The process further includes determining, by a large-movement detection sub-module, a large movement of the living thing based on the first pre-processed result and filtering, by a second pre-process sub-module, the first pre-processed result using a second low-pass filter. The process yet includes generating, by a second pre-process sub-module, a second pre-processed result by down sampling the returned radio signals using a first digital down-converter and determining, by a micro-movement detection sub-module, a micro movement of the living thing based on the second pre-processed result. The process still includes generating, transforming, by a breath and heartbeat detection sub-module, the second pre-processed result to frequency domain and determining, by the breath and heartbeat detection module, if an energy level of the second pre-processed result within a predetermined frequency range is higher than a predetermined level. The process further includes determining, by a presence determination sub-module, the presence of the living thing based on the determination of the large movement, the micro movement, and the breath or heartbeat determined by the corresponding determination sub-module.

It is to be understood that both the foregoing general description and the following detailed description are exemplary and explanatory only and are not restrictive of the invention, as claimed.

DETAILED DESCRIPTION

Figure 1:
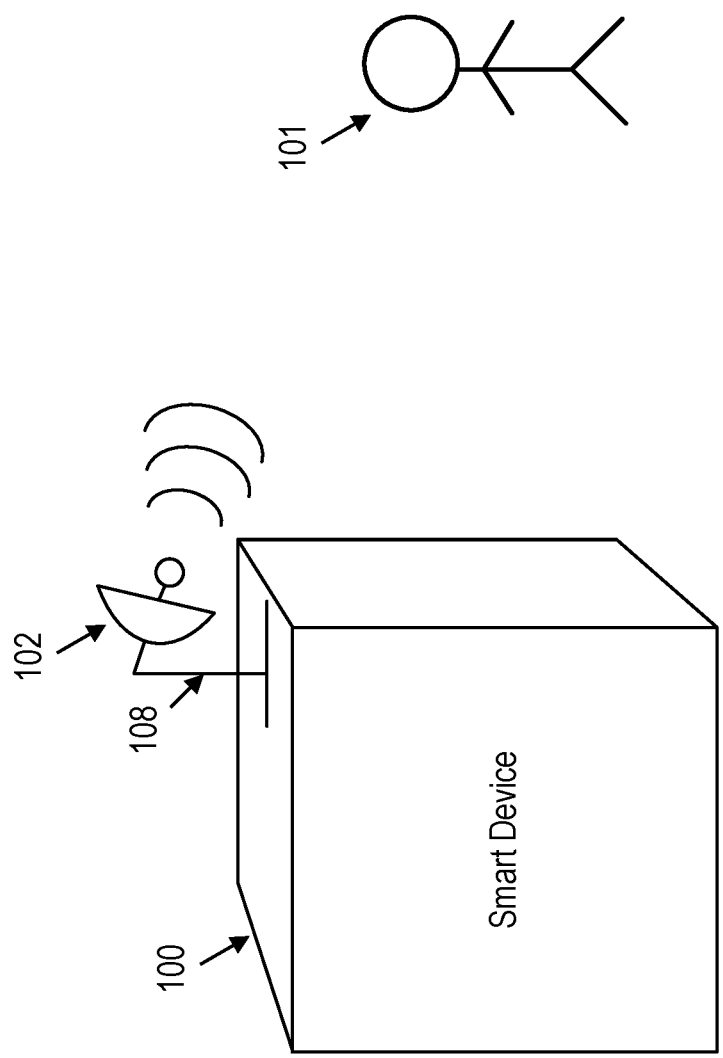
FIG. 1 illustrates a schematic diagram of an exemplary smart device equipped with an exemplary Radar system implementing an improved detection method, according to embodiments of the present disclosure.

Reference will now be made in detail to the exemplary embodiments, examples of which are illustrated in the accompanying drawings. Wherever possible, the same reference numbers will be used throughout the drawings to refer to the same or like parts.

The radio detection system (e.g., a Radar system) may be used to detect objects. Besides the common application of the detecting result, such as the speed and/or location of a vehicle, the vacancy of a parking spot, etc., the detecting result can also be used for human activities monitoring, such as detecting the presence/existence of a human being. For example, the radio detection system may include a transmitter (e.g., a transmitter antenna) configured to emit electromagnetic waves (e.g., continuous or pulsed) to illuminate the environment around the radio detection system and may also include a receiver (e.g., a receiving antenna) configured to receive the returned electromagnetic waves reflected by the objects. The radio detection system may further include a processing module configured to control the emitting and receiving of the electromagnetic waves and to process the received electromagnetic waves respectively. Based on analyzing the frequency difference between the emitted and the received/returned electromagnetic waves (e.g., according to Doppler shift), the moving speed, properties, and/or the movements (e.g., large, micro, or movements at certain frequencies) of a living being can be determined.

When using a radio detection system to detect the presence of the living thing (e.g., in a security system or in home automation applications), the system needs to react fast and accurate while taking low electrical power and computing resources. Conventional living thing presence detection methods determine the presence of the living thing focusing on detecting the breath and/or heartbeat of the living thing. Those methods suffer from different problems. Concretely, when using hardware filtering for processing the reflected signals (e.g., the returned radio signals), the core circuit design may be complicated. For example, in order to filter the noise in a cascade manner, the core circuit needs to include at least an amplifier circuit, a low-pass filter circuit, and a high-pass filter circuit with predetermined parameters. For methods applying Fast Fourier transform (FFT) to the whole bandwidth of the detected signal, the methods normally are complicated, and are time and computational resource consuming. Accordingly, those methods are less desirable because the living thing presence detection requires for a fast or even instantaneous response to the presence of the detection subject (e.g., the living thing), and thus needs to be simple in processing the detect signal.

As will be disclosed in detail below, the radio detection system disclosed herein implements an improved method/mechanism to address the above-mentioned problems in living thing presence detection.

In some embodiments, the radio detection system may include a processing module that includes a large-movement detection sub-module configured to detect if there is any large movements (e.g., walking, jumping, and/or running) of a living thing, a micro-movement detection sub-module configured to detect if there is any micro-movements (e.g., facial expressions, keyboard striking, writing, etc.) of the living thing, and a breath and heartbeat detection sub-module configured to detect micro-movements of a living thing at a relatively constant rhythm (e.g., micro-movements at substantially a constant frequency) such as heartbeat and/or breath of the living thing. The improved detection mechanism may include detecting the presence of the living thing based on considering the determinations of all three sub-modules. For example, if any one of the determinations of the three sub-modules is "YES", namely, if there is at least one of the large movement, the micro movement, and/or the beath/heartbeat of the living thing being detected by the corresponding sub-module, the system may determine that there is a living thing being present and further instructions (e.g., control signals) such as open the light, setup the alarm, contact the local authority (e.g., the police) etc., may be determined and transmitted to control the smart device accordingly.

By combining the detection result of different detection sub-modules disclosed herein, the radar system can detect the presence of the living thing both fast and accurate. Concretely, the large-movement detection sub-module can detect any large movement of the living thing by applying a sliding window algorithm to received signals (e.g., the signals reflected from the environment) in about 200 milliseconds. However, it may suffer from a lot of different interferences/disruptions while detecting. For example, a fallen leaf or a moving car may interfere/disrupt the detection of the large-movement detection sub-module. Accordingly, the large-movement detection sub-module may be the fastest but the least accurate detection sub-module among all the three detection sub-modules.

On the other hand, the micro-movement detection sub-module can detect any micro movement of the living thing by applying a sliding window algorithm to the reflected signals in about 3 seconds to 10 seconds. Thus, the micro-movement detection sub-module may be more accurate than the large-movement detection sub-module while being more time consuming in detection.

Additionally, the breath and heartbeat detection sub-module can detect any breath/heartbeat of the living thing by applying frequency analysis within a predetermined frequency range to the reflected signal to detect substantially repetitive movements at certain frequency ranges. Therefore, the breath and heartbeat detection sub-module can be the most and would be the most robust to noises among all the three detection sub-modules. However, the breath and heartbeat detection sub-module may be the most computational resources and time consuming among all the three detection sub-modules because of the determination mechanism (e.g., applying frequency analysis to the received signal within a predetermined frequency range). Also, the breath and heartbeat detection sub-module has the highest requirement of the hardware among all the three detection sub-modules (e.g., requires the highest sensitivity of the transmitter/receiver module).

Because the system disclosed herein combines the detection results from different detection sub-modules for determining the presence of the living things, the system can leverage the advantages of all the detection sub-modules at the same time. As a result, the detection can be precise while being fast in processing time. Additionally, when determine the substantially repetitive movements at certain frequency ranges (e.g., the breath/heartbeat of the living thing), the breath and heartbeat detection sub-module only apply frequency analysis to the received signal (e.g., apply FFT to the received signal) within a predetermined frequency range (e.g., between about 0.1 Hz to about 0.6 Hz to coincide with the frequency of the breath/heartbeat of the living thing). This could further reduce the complexity of the breath/heartbeat detection comparing to the existing living thing detection methods.

It is understood that any possible combinations (e.g., any two or all three) of the disclosed detection sub-modules or various modifications to the disclosed system and the related methods should be apparent to those skilled in the art from consideration of the specification disclosed herein. Other embodiments will be apparent to those skilled in the art from consideration of the specification disclosed herein and practice of the system and related methods disclosed below. For example, it is contemplated that although all three detection sub-modules are disclosed herein as an integral part of the radio detection system, and the improved method disclosed herein includes making the detection based on all three determinations of the corresponding sub-modules, not all three of them are necessary. Using any combinations of determinations of the three detection sub-modules should be apparent to those skilled in the art from consideration of the specification disclosed herein. Specifically, the improved method may only include considering if a large-movement and/or a micro-movement is detected, or if a large-movement and/or a beath and/or heartbeat is detected, etc. Accordingly, the radio system may include only the corresponding detection sub-modules for determining the detection result.

In some embodiments, to further make the detection less complicated and more computational resource saving, when processing the received signals (e.g., the radio signals returned from the environment), the processing module may include a first pre-process sub-module for pre-processing the received signal before processing the received signal by any detection sub-modules disclosed herein. The first pre-process module may include a first low-pass filter and a first digital down-converter configured to generate a first pre-processed result by down sampling the received signal at a first down sampling rate.

In some embodiments, the processing module may further include a second pre-process sub-module configured to further pre-process the first pre-processed result received from the first pre-process sub-module before processing the received signal by the micro-movement detection sub-module and/or the breath and heartbeat detection sub-module. The second pre-process sub-module may include a second low-pass filter and a second digital down-converter to generate a second pre-processed result by further down sampling the first pre-processed result at a second down sampling rate lower than the first down sampling rate.

It is intended that the specification and examples be considered as exemplary only, with a true scope being indicated by the following claims and their equivalents.

When being used in the above-mentioned applications (e.g., to aid home automation or premises security), the radio detection system can be equipped on smart devices such as smart air conditioners (AC), smart televisions (TVs), etc., or illumination devices' such as lights in a back yard or search lights. The radio detection system can be used for detecting the existence of living things (e.g., human beings, pets, and/or wild animals) and/or the condition of the living beings (e.g., the pulse, the heartbeat, the breath, etc.) where the detecting result can be used to control the device accordingly. For example, FIG. 1 illustrates a schematic diagram of an exemplary smart device equipped with a radar system implementing improved methods for detecting presence of a living thing, according to embodiments of the present disclosure. Consistent with some embodiments, smart device 100 may be a smart AC configured for controlling the room condition (e.g., the temperature and/or the humidity) based on the presence and/or condition of the detected living thing (e.g., whether the human being or pet is sleeping), determined by the Radar system implementing the improved method for living thing presence detection. It is contemplated that smart device 100 may also be other devices that can react to/be adjusted according to the presence of a living thing automatically.

As illustrated in FIG. 1, smart device 100 may be equipped with a Radar system implementing improved methods 102 (also referred to as "Radar system 102" hereinafter) for detecting presence of a living thing 101. In some embodiments, Radar system 102 may be mounted to a body of smart device 100 via a mounting structure 108. Mounting structure 108 may be an electro-mechanical device installed or otherwise attached to the body of smart device 100. In some embodiments of the present disclosure, mounting structure 108 may use screws, adhesives, or another mounting mechanism. It is contemplated that the manners in which Radar system 102 can be equipped on smart device 100 are not limited by the example shown in FIG. 1 and may be modified depending on the types of Radar system and/or smart device 100 to achieve desirable radio detecting performance.

Consistent with some embodiments, Radar system 102 may be configured to capture data as smart device 100 performs its functions. For example, a transmitter of Radar system 102 may be configured to scan the surrounding environment. Radar system 102 measures movements/presence of a target by illuminating the target with electromagnetic waves (e.g., a wireless signal) and measuring the reflected/scattered electromagnetic waves (e.g., the echo) with a receiver. In some embodiments, the electromagnetic waves used for Radar system 102 may be around 5.8 GHz and may be pulsed or continuous electromagnetic waves. In some embodiments of the present disclosure, Radar system 102 may capture information such as large-movements, micro-movements, and/or breath and heartbeat of living thing 101 to determine the presence and/or the condition of living thing 101 (e.g., whether living thing 101 is within the room and/or whether living thing 101 is sleeping) based on Doppler shift of the echo. The gathered information may be used for automatic controlling of the functioning of smart device 100.

Figure 2:
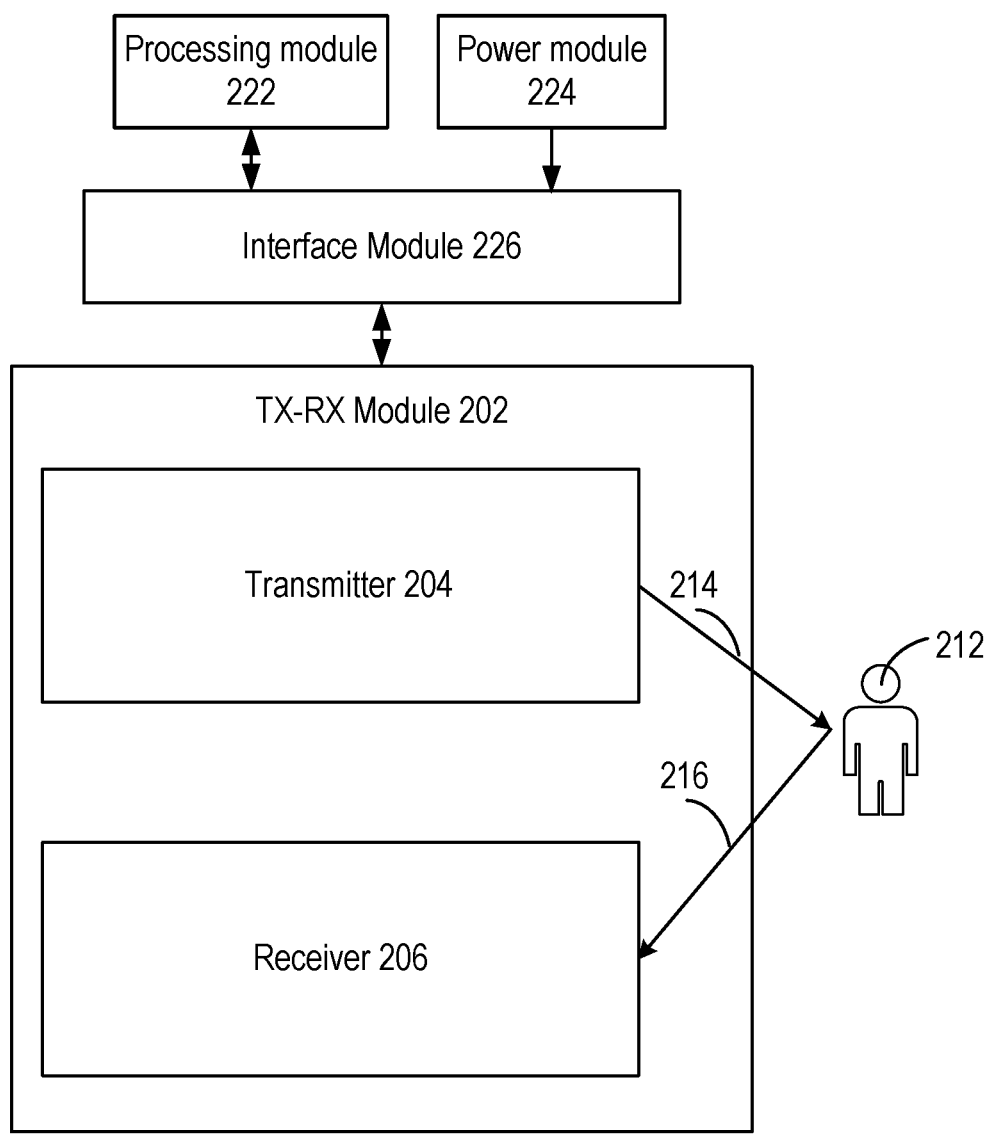
FIG. 2 illustrates a schematic diagram of an exemplary Radar system implementing an improved detection method, according to embodiments of the present disclosure.

FIG. 2 illustrates a block diagram of an exemplary Radar system 200 implementing improved methods for detecting presence of a living thing (e.g., living thing 101 in FIG. 1), according to embodiments of the present disclosure. Radar system 200 may be the same as Radar system 102 shown in FIG. 1. As illustrated, Radar system 200 may include an integrated transmitter/receiver module 202 that includes a transmitter antenna 204 ("transmitter 204" hereinafter) and a receiver antenna 206 ("receiver 206" hereinafter). In some embodiments, transmitter 204 and receiver 206 are integrated on a single substrate. For example, integrated transmitter/receiver module 202 may include a printed circuit board (PCB) for providing mechanical base support and electrical interfaces that facilitate electrical communication amongst some/all parts in the integrated transmitter/receiver module 202 such as transmitter 204 and receiver 206. In some embodiments, transmitter 204 and receiver 206 may be microstrip/patch antennas etched on a first side of a dielectric substrate of the PCB and may be connected through a chip (e.g., a processing module 222) for data processing and controlling. For better illustrative purposes, transmitter 204 and receiver 206 shown in FIG. 1 only include one pair of transmitter antenna and/or receiver antenna respectively. It is understood that transmitter 204 and receiver 206 may include more than one transmitter antenna and/or receiver antenna respectively for achieving desirable detecting performance.

In some embodiments, each of transmitter 204 and receiver 206 may include radiation boundaries and non-radiation boundaries. Specifically, transmitter 204 may emit electromagnetic waves 214 to an object 212 (e.g., a living thing) mostly through radiation boundaries of transmitter 204. Echoes (e.g., returned/reflected electromagnetic waves 216 reflected by object 212) may be received by receiver 206 mostly through radiation boundaries of receiver 206. In some embodiments, object 212 within the range of detection may be made of a wide range of materials including, for example, non-metallic objects, rocks, rain, chemical compounds, aerosols, clouds and even living things.

Receiver 206 may be configured to detect returned electromagnetic wave 216 returned from object 212. Upon contact, electromagnetic waves can be reflected/scattered by object 212 via scatterings. Returned electromagnetic wave 216 may be in a same or different direction from electromagnetic wave 214. Returned electromagnetic wave 216 may have the same or different waveform (e.g., bandwidth and wavelength) as those in electromagnetic wave 214. In some embodiments, upon receiving returned electromagnetic wave 216 from the surrounding environment (e.g., reflected by object 212), receiver 206 may output electrical signals reflecting the property of returned electromagnetic wave 216 (e.g., bandwidth and wavelength). Based on the time for electromagnetic wave 214 to move forward and the time for returned electromagnetic wave 216 to move backward, and/or the Doppler shift between electromagnetic wave 214 and returned electromagnetic wave 216, position, speed, and/or other properties of object 212 may be detected.

In some embodiments, Radar system 200 may further include processing module 222. Specifically, in some embodiments, processing module 222 may include a processor (will be discussed in detail in connection with FIGS. 3, 4, 5, and 6 below) and a non-transitory computer-readable medium (discussed in detail in connection with FIG. 7) for processing the signal collected by integrated transmitter/receiver module 202, and a power module 224 for providing power supply to the system. For instance, processing module 222 may control transmitter 204 to transmit/emit electromagnetic wave 214 and receiver 206 to receive/detect returned electromagnetic wave 216. In some embodiments, processing module 222 may also implement data acquisition and analysis. For instance, processing module 222 may collect digitalized signal information from a readout circuit (not shown) connected to receiver 206, detect the distance/speed/large movement/micro movement (e.g., vibration) of object 212 according to the travel time, frequency, and/or wavelength of electromagnetic waves shift between electromagnetic waves 214 and returned electromagnetic waves 216, and determine the condition/property/characteristic of object 212 (e.g., whether object 212 is a living thing) based on the detection result.

In some embodiments, power module 224 may be configured to provide electrical power to modules such as integrated transmitter/receiver module 202 and/or processing module 222. In some embodiments, power module 224 may include a DC power supply, an AC power supply, or any other power supply that can provide suitable voltage, current, and frequency to electrically power the modules.

In some embodiments, to facilitate the communication (e.g., transmission of control signals and/or data) between and among the modules and/or with an outside device (e.g., a manifestation device), Radar detection system 200 may further include an interface module 226 operatively connecting acquisition modules such as integrated transmitter/receiver module 202 to processing module 222 for transmitting data. Integrated transmitter/receiver module 202 and/or processing module 222 may also be electrically connected to power module 224 through interface module 226 for receiving electrical power. For example, instead of having interfaces for transmitting data and/or receiving electrical power on each module individually, modules such as integrated transmitter/receiver module 202 and/or processing module 222 may share the interface circuits integrated on interface module 226. This can further free up the space occupied by those modules and increase the data and/or power transmission efficiency. Interface module 226 may also increase the robustness of data transmission. In some embodiments, interface module 226 may further be connected to an external connector of an outside device for further processing or manifesting the data.

It is contemplated that in some embodiments, processing module 222, power module 224, and/or interface module 226 may be positioned to predetermined positions of Radar system 200 by being affixed to the PCB of integrated transmitter-receiver 202. It is also contemplated that in some other embodiments, any of processing module 222, power module 224, and/or interface module 226 may not be part of Radar system 200 or may be positioned at other locations, separate from Radar system 200 to achieve desired effect.

Figure 3:
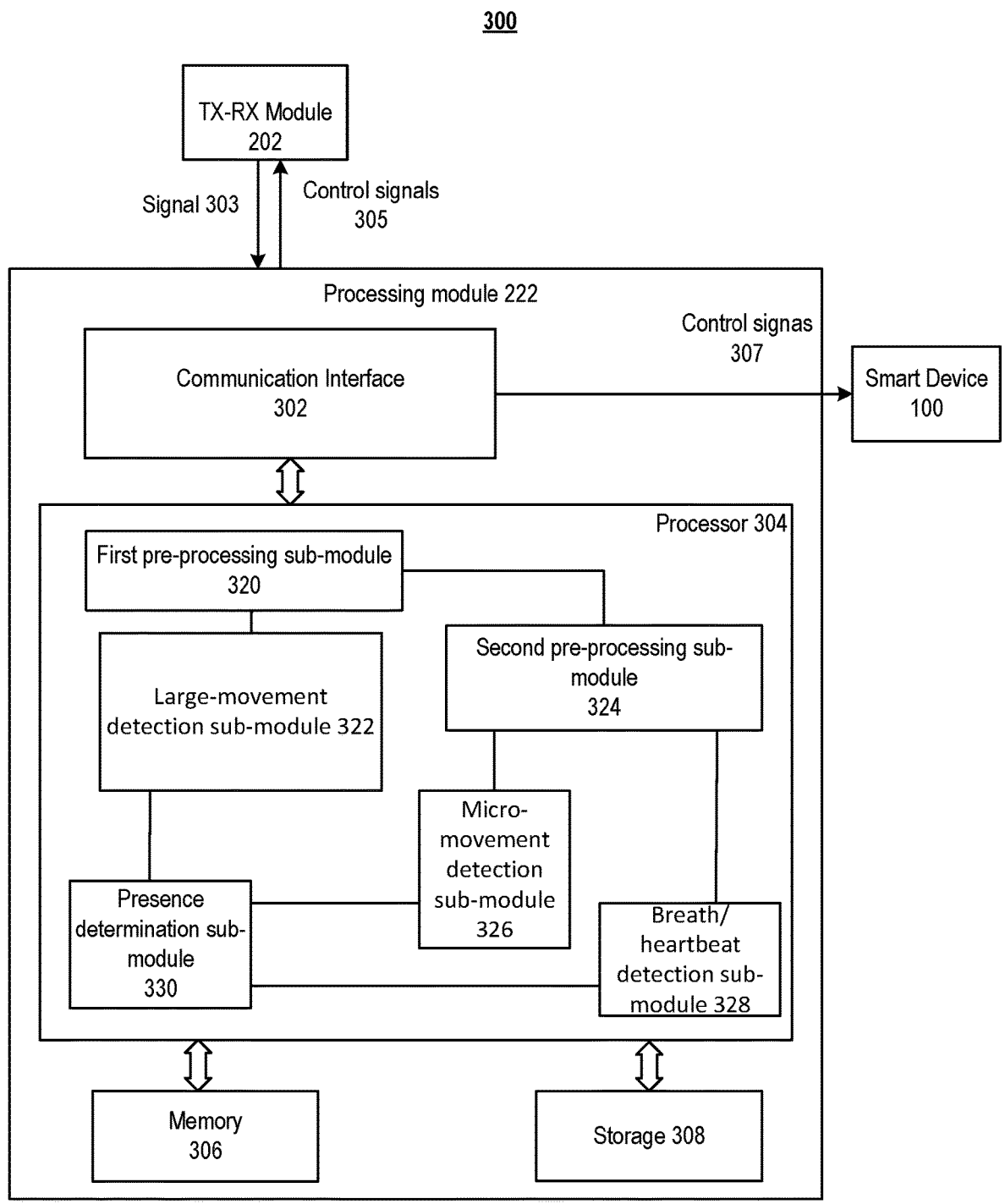
FIG. 3 illustrates a block diagram of an exemplary Radar system implementing the improved detection method, according to embodiments of the present disclosure.

FIG. 3 illustrates a block diagram of an exemplary processing module 300 in a Radar system implementing the improved living thing presence detection method, according to embodiments of the disclosure. Consistent with the present disclosure, processing module 300 may be an embodiment of processing module 222 in Radar system 200 as shown in FIG. 2. In some embodiments, as shown in FIG. 3, processing module 300 may include a communication interface 302, a processor 304, a memory 306, and a storage 308. In some embodiments, processing module 300 may have different modules in a single device, such as an integrated circuit (IC) chip (e.g., implemented as an application-specific integrated circuit (ASIC) or a field-programmable gate array (FPGA)), or separate devices with dedicated functions. In some embodiments, one or more components of processing module 300 may be located in a cloud or may be alternatively in a single location (such as inside a user equipment e.g., smart device 100) or distributed locations. Components of processing module 300 may be in an integrated device or distributed at different locations but communicate with each other through a network (not shown). Consistent with the president disclosure, processing module 300 may be configured to determine the presence of a living thing based on processing/analyzing the detected result (e.g., reflected signal 303) detected/received by the receiver of transmitter/receiver module 202. The determination of the presence of a living thing may be provided to smart device 100 for further processing and/or used for generating control signals for controlling smart device 100.

Communication interface 302 may send data to and receive data from components such as transmitter/receiver module 202 via communication cables, a Wireless Local Area Network (WLAN), a Wide Area Network (WAN), wireless networks such as radio signals, a cellular network, and/or a local or short-range wireless network (e.g., Bluetooth™), or other communication methods. In some embodiments, communication interface 302 may include an integrated services digital network (ISDN) card, cable modem, satellite modem, or a modem to provide a data communication connection. As another example, communication interface 302 may include a local area network (LAN) card to provide a data communication connection to a compatible LAN. Wireless links can also be implemented by communication interface 302. In such an implementation, communication interface 302 can send and receive electrical, electromagnetic or optical signals that carry digital data streams representing various types of information.

Consistent with some embodiments, communication interface 302 may receive signal 303 (e.g., returned electromagnetic wave 216 as shown in FIG. 2). In some embodiments, signal 303 may be received by transmitter/receiver module 202. In some embodiments, communication interface 302 may further provide the received data (e.g., signal 303) to memory 306 and/or storage 308 for storage or to processor 304 for processing. In some embodiments, processor 304 may generate and transmit control signals 305 for controlling transmitter/receiver module 202 detect/scan the environment and may determine the presence of a live thing based on signal 303. Processor 304 may also generate control instructions 307 for controlling smart device 100 to perform functions.

Processor 304 may include any appropriate type of general-purpose or special-purpose microprocessor, digital signal processor, or microcontroller. Processor 304 may be configured as a separate processor module dedicated to performing living thing presence detection. Alternatively, processor 304 may be configured as a shared processor module for performing other functions in addition to living thing presence detection.

Memory 306 and storage 308 may include any appropriate type of mass storage provided to store any type of information that processor 304 may need to operate. Memory 306 and storage 308 may be a volatile or non-volatile, magnetic, semiconductor, tape, optical, removable, non-removable, or other type of storage device or tangible (i.e., non-transitory) computer-readable medium including, but not limited to, a ROM, a flash memory, a dynamic RAM, and a static RAM. Memory 306 and/or storage 308 may be configured to store one or more computer programs that may be executed by processor 304 to perform functions disclosed herein. For example, memory 306 and/or storage 308 may be configured to store program(s) that may be executed by processor 304 to detect the presence of the living thing.

As shown in FIG. 3, processor 304 may include multiple modules, such as, a large-movement detection sub-module 322 configured to detect if there is any large movements (e.g., walking, jumping, and/or running) of a living thing, a micro-movement detection sub-module 326 configured to detect if there is any micro-movements (e.g., facial expressions, keyboard striking, writing, etc.) of the living thing, a breath and heartbeat detection sub-module 328 configured to detect micro-movements of a living thing at a certain rhythm (e.g., micro-movements at substantially a constant frequency) such as heartbeat and/or breath of the living thing, presence determination sub-module 330 configured to determine the presence of the living thing based on the determination of the large movement, the micro movement, and the breath or heartbeat determined by the corresponding determination sub-module and the like. In some embodiments, a first pre-process sub-module 320 and a second pre-process sub-module 324 for pre-processing signal 303 (e.g., down sampling the signal rate of signal 303) to make the detection less complicated and more computational resource economical.

As will be disclosed in detail below (e.g., along with the description of FIGS. 4, 5, and 6), sub-modules 320-330 (and any corresponding sub-modules or sub-units) can be hardware units (e.g., portions of an integrated circuit) of processor 304 designed for use with other components or software units implemented by processor 304 through executing at least part of a program. The program may be stored on a computer-readable medium, and when executed by processor 304, it may perform one or more functions. Although FIG. 3 shows sub-modules 320-330 all within one processor 304, it is contemplated that these units may be distributed among different processors located closely or remotely with each other.

Figure 4:
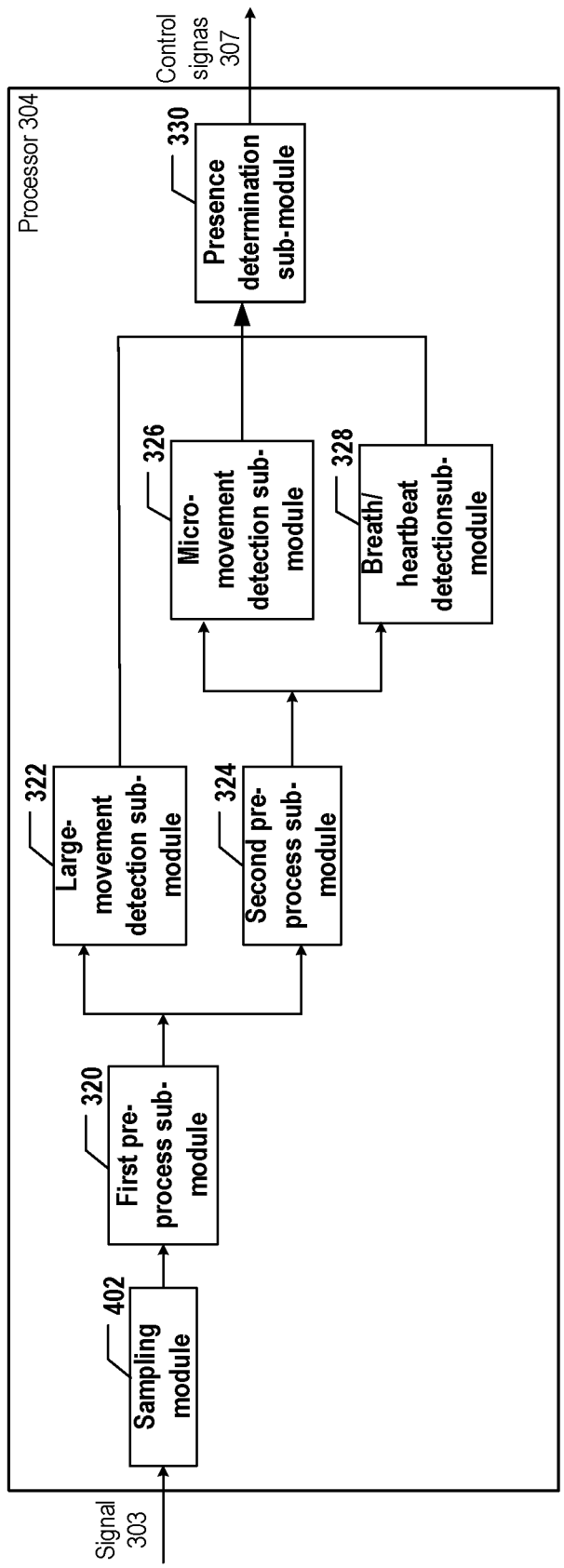
FIG. 4 illustrates a block diagram of an exemplary processor of a Radar system implementing the improved living thing presence detection method, according to embodiments of the present disclosure.
Figure 5:
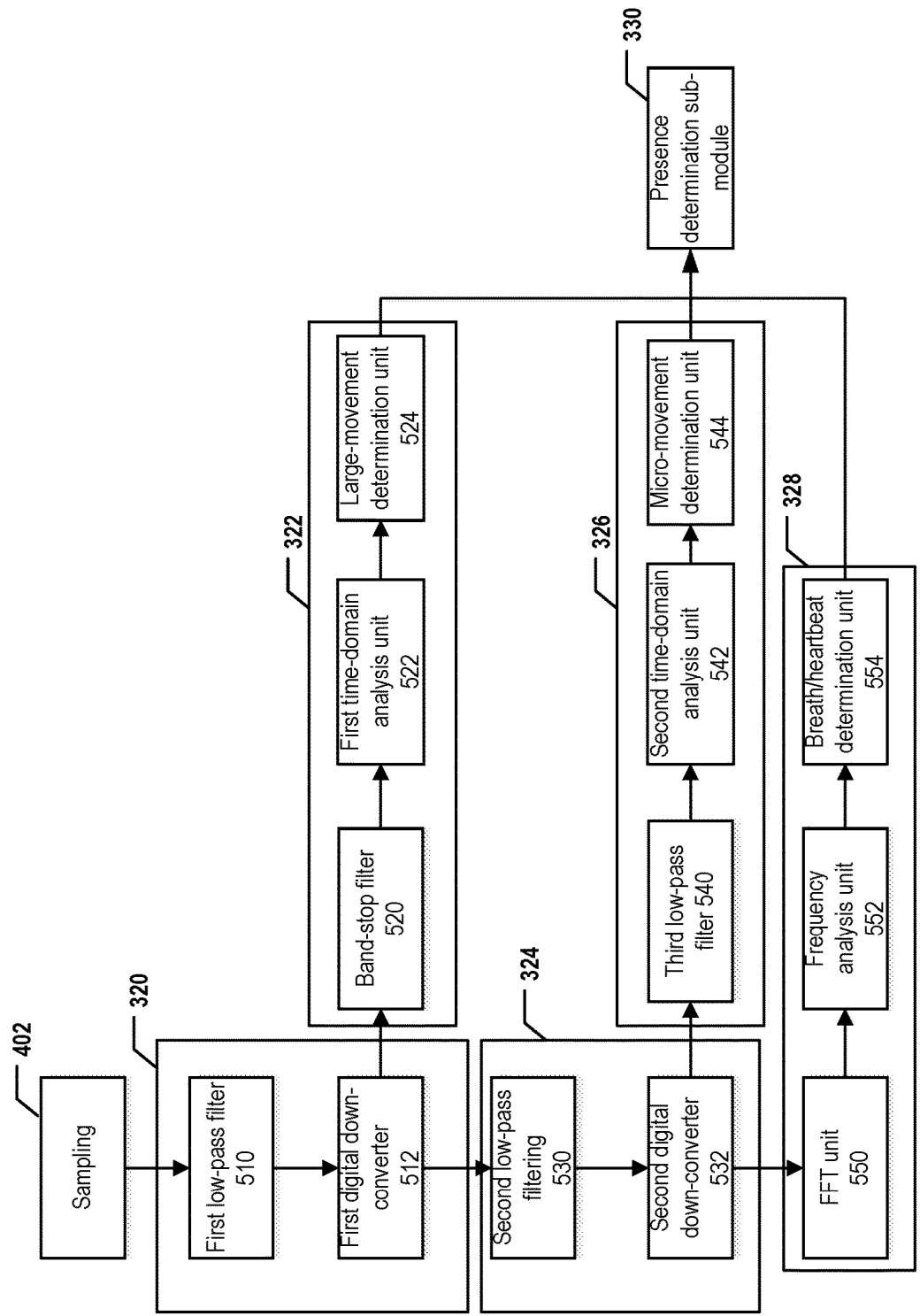
FIG. 5 illustrates a detailed block diagram of an exemplary processor of a Radar system implementing the improved living thing presence detection method, according to embodiments of the present disclosure.
Figure 6:
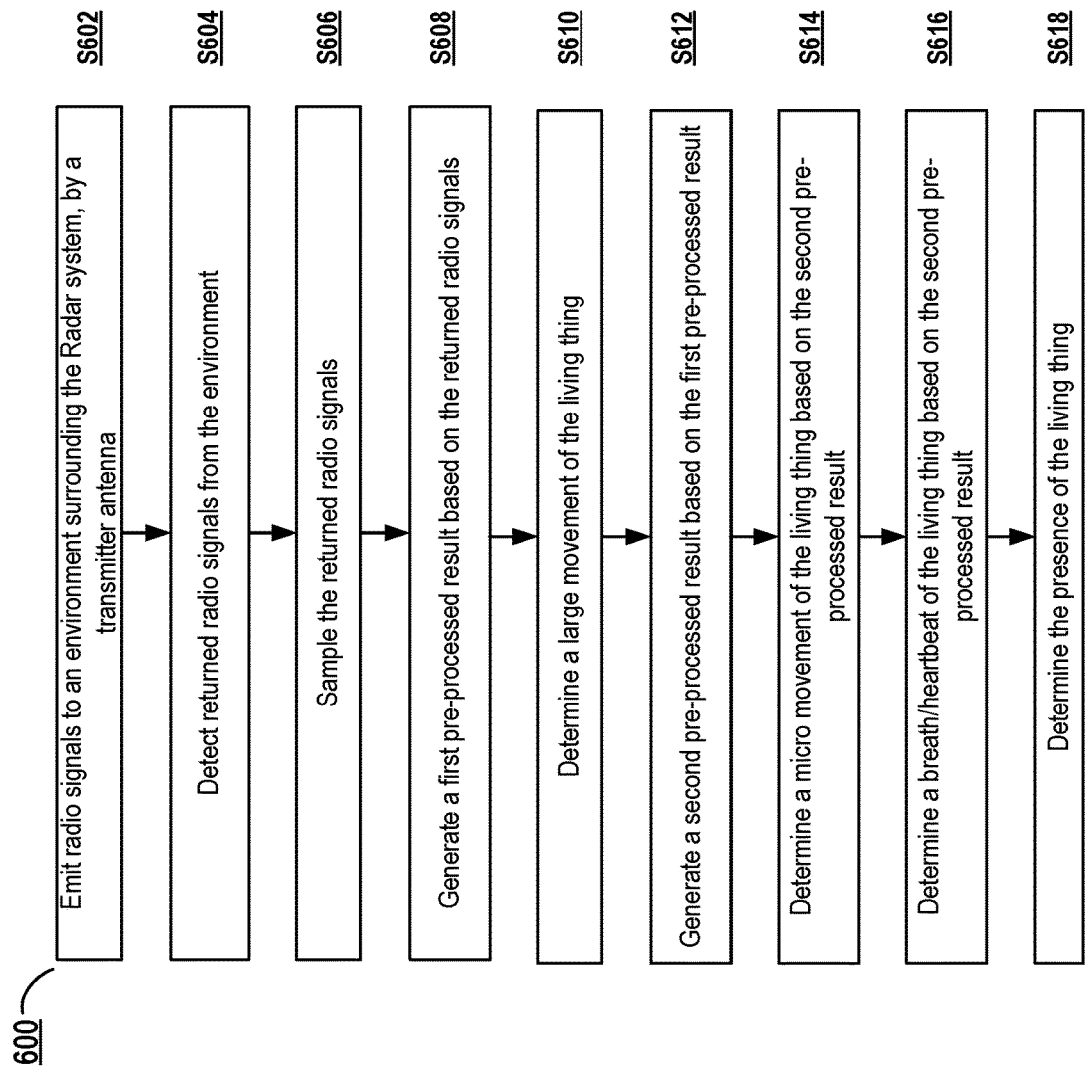
FIG. 6 illustrates a flow chart of an exemplary method of improved living thing presence detection performed by a Radar system, according to embodiments of the present disclosure.

Specifically, FIG. 4 illustrates a block diagram of exemplary processor 304 of Radar system 200 implementing an improved living thing presence detection method and FIG. 5 illustrates a detailed block diagram of exemplary processor 304, according to embodiments of the present disclosure. Sub-modules 320-330 are configured to determine the presence of the living thing based on signal 303. In some embodiments, sub-module 320-330 of FIGS. 4 and 5 may execute computer instructions to perform living thing presence detection. For example, FIG. 6 illustrates a flowchart of an exemplary method 600 for living thing presence detection performed by Radar system 200, according to embodiments of the disclosure. Method 600 may include steps S602-S620 as described below. It is to be appreciated that some of the steps may be optional to perform the disclosure provided herein. Further, some of the steps may be performed simultaneously, or in a different order than shown in FIG. 6.

In step 602, electromagnetic waves (e.g., radio signals) may be emitted to an environment surrounding the Radar system for detecting the presence of a living thing. For example, a transmitter/receiver module (e.g., transmitter/ receiver module 202) may emit the electromagnetic waves (e.g., emitted by a transmitter antenna) to the environment surrounding the Radar system for detecting living things. In some embodiments, the transmitter/receiver module may be controlled by a processor (e.g., processing module 222 and/or processor 304) for desired performance. For example, the transmitter/receiver module may have a static field of view (FOV) coving a predetermined filed (e.g., a backyard) and the processor may control the on/off of the transmitter/receiver module. For another example, the transmitter/receiver module may be controlled by the processor to scan the FOV to form a dynamic FOV.

In step S604, the returned radio signals (e.g., signal 303) may be the detected/received. For example, transmitter/receiver module may detect/receive the returned radio signals (e.g., detected by a receiver antenna) and transmit the returned radio signals (e.g., signal 303) to a processor (e.g., processor 304) for living thing presence detection.

Upon receiving signal 303, in step S606, signal 303 may be sampled. For example, as illustrated in FIGS. 4 and 5, a sampling module 402 may be configured to sample signal 303 at a predetermined sampling rate (e.g., 635 Hz) for a certain valid signal collection range (e.g., lower than 317 Hz for living thing presence detection). In some embodiments, sampling module 402 may include components of or being part of an Integrated Circuits Chip (IC Chip). For example, sampling module 402 may include an analog-digital-convertor (ADC) for obtaining the signal (e.g., signal 303) and may transmit the processed signal to designated cache through direct memory access (DMA) for further processing.

In step S608, a first pre-processed result may be generated by further pre-processing signal 303 using first pre-process sub-module 320. For example, as illustrated in FIG. 4, first pre-process sub-module 320 may generate the first pre-processed result by filtering the returned signal 303 using a first low-pass filter and by down sampling signal 303 using a first digital down-converter. Specifically, as illustrated in FIG. 5, first pre-process sub-module 320 may include a first low-pass filter 510 (e.g., having a cut-off frequency around about 130 Hz) configured to filter high frequency noises such as utility frequency signals and/or multiple harmonic signals out, and a first digital down-convertor 512 configured to down sampling the signal. In some embodiments, first digital down-convertor 512 may include a second order Cascaded Integrator Comb (CIC) configured to down sample signal 303 (e.g., from 635 Hz to 317.5 Hz) and filter out a portion of the high frequency noise.

In step S610, a large movement of the living thing may be determined based on the first pre-processed result. For example, as illustrated in FIG. 4, large-movement detection sub-module 322 may determine the large movement of the living thing based on the first pre-processed result. Specifically, large-movement detection sub-module 322 may receive the first pre-processed result from first pre-process sub-module 320, filter out noises within a certain frequency band from the first pre-processed result, filter out mutations in the first pre-processed result based on time-domain analysis of the first pre-processed result, and determine the large movement of the living thing based on applying a first sliding window algorithm to the filtered first pre-processed result.

Specifically, as illustrated in FIG. 5, in some embodiments, large-movement detection sub-module 322 may include a band-stop filter 520 configured to filter out noises within a certain frequency band from the first pre-processed result. For example, band-stop filter 520 may filter signals with a frequency between about 50 Hz to about 60 Hz and/or a frequency between 100 Hz to about 120 Hz. In some embodiments, large-movement detection sub-module 322 may also include a first time-domain analysis unit 522 configured to further filter out mutations in the first pre-processed result based on time-domain analysis of the first pre-processed result. In some embodiments, large-movement detection sub-module 322 may further include a large-movement determination unit 524 configured to determine the large movement of the living thing based on applying a first sliding window algorithm to the filtered first pre-processed result. In some embodiments, large-movement determination unit 524 may be configured to determine at least one of an amplitude or a value range of the filtered first pre-processed result processed/filtered by band-stop filter 520 and first time-domain analysis unit 522.

Specifically, when performing the first sliding window algorithm on the filtered first pre-processed result, large-movement determination unit 324 may divide the filtered first pre-processed result into multiple frames based on the first sliding window algorithm, determine a value range of the filtered first pre-processed result in each frame of the filtered first pre-processed result, and determine the large movement of the living thing. For example, large-movement determination unit 324 may determine that the large movement of the living thing is detected if the value range is higher than a first predetermined threshold.

In step S612, a second pre-processed result may be generated by further pre-processing signal 303 using second pre-process sub-module 324 based on the first pre-processed result received from first pre-process sub-module 320. For example, as illustrated in FIG. 4, second pre-process sub-module 324 may generate the second pre-processed result by filtering the first pre-processed result using a second low-pass filter and by down sampling signal 303 using a second digital down-converter.

Specifically, as illustrated in FIG. 5, second pre-process sub-module 324 may include a second low-pass filter 530 having a cut-off frequency lower than the cut-off frequency of first low-pass filter 510 (e.g., having a cut-off frequency around about 30 Hz). Second pre-process sub-module 324 may also include a second digital down-convertor 532 configured to down sampling the first pre-processed result. In some embodiments, first digital down-convertor 512 may include a thirteen order Cascaded Integrator Comb (CIC) configured to down sample the first pre-processed result (e.g., from 317.5 Hz to 24.4 Hz).

In step S614, a micro-movement of the living thing may be determined based on the second pre-processed result. For example, as illustrated in FIG. 4, micro-movement detection sub-module 326 may determine the micro movement of the living thing based on the second pre-processed result. Specifically, micro-movement detection sub-module 326 may receive the second pre-processed result from second pre-process sub-module 324, filter out noises below a certain frequency from the second pre-processed result, filter out mutations in the first pre-processed result based on time-domain analysis of the first pre-processed result, and determine the large movement of the living thing based on applying a second sliding window algorithm to the filtered first pre-processed result.

Specifically, as illustrated in FIG. 5, in some embodiments, micro-movement detection sub-module 326 may include a third low-pass filter 540 configured to filter out noises below a predetermined frequency from the first pre-processed result. For example, when the movement of the chest of the living thing caused by breathing (e.g., the ups and downs of the chest having a frequency between about 0.1 Hz to about 0.6 Hz) is the micro movement being considered for living thing presence detection, the cut-off frequency of third low-pass filter 540 may be set to be about around 0.6 Hz (e.g., approximate to the breathing of the living thing) to filter out any higher than 0.6 Hz signal components of signal 303. It is contemplated that the considered micro movement may not be limited to the breath of the living thing. Other movements such as facial expressions, keyboard striking, writing, etc. may also be configured as the micro movement to be detected. Accordingly, the cut-off frequency of third low-pass filter 540 may be adjust to/set as the corresponding frequency to achieve desired performance.

In some embodiments, micro-movement detection sub-module 326 may also include a second time-domain analysis unit 542 configured to further filter out mutations in the first pre-processed result based on time-domain analysis of the first pre-processed result. In some embodiments, micro-movement detection sub-module 326 may further include a micro-movement determination unit 544 configured to determine the micro movement of the living thing based on applying a second sliding window algorithm to the filtered first pre-processed result. In some embodiments, micro-movement determination unit 326 may be configured to determine at least one of an amplitude or a value range of the filtered first pre-processed result processed/filtered by third low-pass filter 540 and second time-domain analysis unit 542.

For example, when performing the second sliding window algorithm to the filtered first pre-processed result, micro-movement determination unit 326 may divide the filtered first pre-processed result into multiple frames based on the second sliding window algorithm, determine a value range of the filtered first pre-processed result in each frame of the filtered first pre-processed result, and determine the large movement if the value range is higher than a second predetermined threshold. For example, if the value range is higher than second pre-determined level, micro-movement determination unit 326 may determine that the micro movement of the living thing is detected.

In step S616, a breath and/or heartbeat of the living thing may be determined based on the second pre-processed result. For example, as illustrated in FIG. 4, breath and heartbeat sub-module 328 may determine the breath and/or heartbeat of the living thing based on the second pre-processed result. Specifically, breath and heartbeat sub-module 328 may receive the second pre-processed result from second pre-process sub-module 324, transform the second pre-processed result to frequency domain, determine the breath frequency of the living thing based on a frequency of signals in the second pre-processed result within a pre-determined frequency range that has maximum energy level, and determine the breath/heart beat of the living thing based on determining if an energy level of the second pre-processed result within the pre-determined frequency range (e.g., determined based on the determined breath frequency) is higher than a third pre-determined level.

Specifically, as illustrated in FIG. 5, in some embodiments, breath and heartbeat sub-module 328 may include a fast Fourier transform (FFT) unit 550 configured to transform the second pre-processed result from time domain to frequency domain based on FFT. Specifically, in some embodiments, to reduce spectral leakage of the time domain signal, a Hamming window function may be applied before performing the FFT on the second pre-processed result. In some embodiments, FFT unit 550 may apply 256 points or 512 points FFT to the second pre-processed result after applying the Hamming window to the second pre-processed result.

In some embodiments, breath and heartbeat sub-module 328 may also include a frequency analysis unit 552 configured to determine the breath frequency of the living thing based on a frequency of signals in the second pre-processed result within a pre-determined frequency range (e.g., between about 0.1 Hz to about 0.6 Hz). For example, the frequency of signal that has maximum energy level may be determined as the frequency of the breath.

In some embodiments, breath and heartbeat sub-module 328 may further include a breath/heartbeat determination unit 554 configured to determine the breath of the living thing based on determining if an energy level of the second pre-processed result within the pre-determined frequency range (e.g., between about 0.1 Hz to about 0.6 Hz) is higher than the third pre-determined level. For example, if the energy level is higher than third pre-determined level, breath and heartbeat sub-module 328 may determine that the breath/heartbeat of the living thing is detected.

In step S618, the presence of the living thing may be determined based on the determination of the large movement, the micro movement, and the breath or heartbeat determined by the corresponding determination sub-module. For example, as illustrated in FIG. 4, presence determination sub-module 330 may determine the presence of the living thing based on the determination of the large movement, the micro movement, and the breath or heartbeat determined by the corresponding determination sub-module. Specifically, if at least one of the detection results is "YES", meaning that at least one of a large movement, a micro movement, or the breath/heartbeat of the living thing is detected, presence determination sub-module 330 may determine the presence of the living thing is detected. In some embodiments, control instructions 307 may be generated based on the determination (e.g., the living thing is present) for controlling smart device 100 to perform functions such as open the light, setup the alarm, contact the local authority (e.g., the police) etc., depending on the desired function to be achieved by smart device 100.

In some embodiments, one or more of the parameters (e.g., the cut-off frequency of low-pass filters 510, 530, and 540, the frequency range of bad-stop filter 520, etc.) may be dynamically adjusted (e.g., using feedback and/or feedforward loop) to achieve desired effect. For example, the frequency of the living thing may be presumed as below about 0.5 Hz, about 0.8 Hz, about 1 Hz, etc., instead of below about 0.6 Hz as disclosed herein. The adjustment of the corresponding parameter(s) of the component(s) would be apparent to a person skilled in the art from consideration of the specification disclosed herein.

In some embodiments, a computer-readable apparatus including a storage medium stores computer-readable and computer-executable instructions that are configured to, when executed by at least one processor apparatus, cause the at least one processor apparatus or another apparatus (e.g., the computerized apparatus) to perform the operations/operations of the method 600. Example components of the computerized apparatus are illustrated in FIG. 7, which are described in more detail below.

Figure 7:
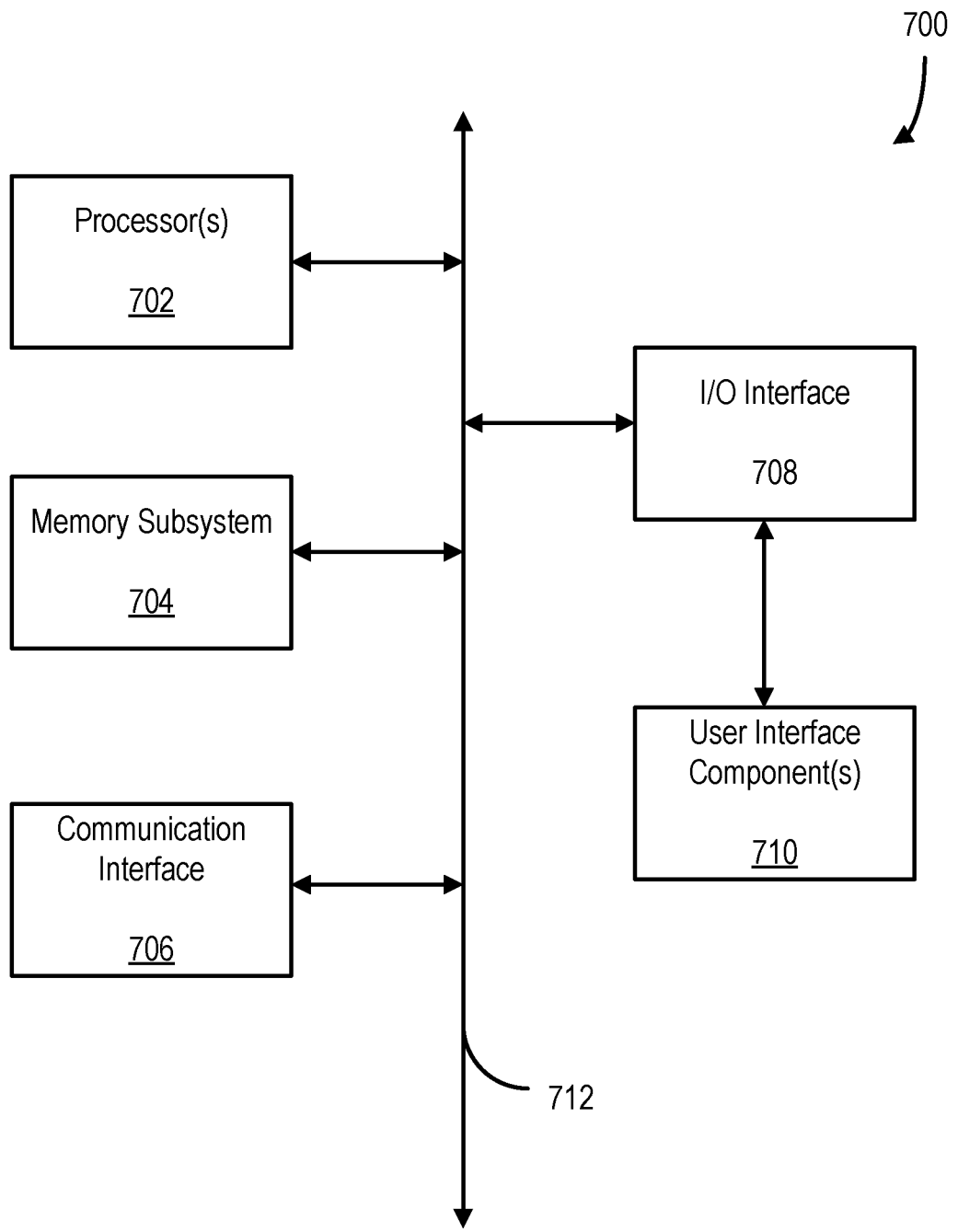
FIG. 7. illustrates a schematic diagram of an example computing device for implementing the methods, systems, and techniques described herein in accordance with some embodiments.

FIG. 7 shows a schematic diagram of components of a computing device 700 that is implemented in a computing system in accordance with some implementations. As illustrated, computing device 700 includes a bus 712 that directly or indirectly couples one or more processors(s) 702, a memory subsystem 704, a communication interface 706, an input/output (I/O) interface 708, and/or one or more user interface components 710. It should be noted that, in some embodiments, various other components are included in a computing device that are not shown in FIG. 7, and/or one or more components shown in FIG. 7 are omitted.

In some embodiments, computing device 700 includes or is coupled to a memory subsystem 704. Memory subsystem 704 includes a computer-readable medium (e.g., non-transitory storage medium) or a combination of computer-readable media. Examples of computer-readable media include optical media (e.g., compact discs, digital video discs, or the like), magnetic media (e.g., hard disks, floppy disks, or the like), semiconductor media (e.g., flash memory, dynamic random access memory (DRAM), static random access memory (SRAM), electrically programmable read-only memory (EPROM), electrically erasable programmable read-only memory (EEPROM), or the like), or a combination thereof. In some embodiments, the computer-readable media includes non-volatile memory, volatile memory, or a combination thereof. In some embodiments, memory subsystem 704 also includes one or more hardware devices such as a solid-state memory, one or more hard drives, one or more optical disk drives, or the like. In some embodiments, memory subsystem 704 stores content files such as text-based files, audio files, image files, and/or video files, etc. In some implementations, the content files include documents, pictures, photos, songs, podcasts, movies, etc. In some embodiments, memory subsystem 704 stores one or more computer program products that are each implemented as a set of instructions (e.g., program code) stored on a computer-readable medium.

A computer program product (e.g., a program stored in or downloadable onto a computer readable medium) includes instructions or program code that are executable by one or more processors (e.g., processor(s) 702, or processor(s) of another computing device communicatively coupled to computing device 700) to perform various operations or functions such as those described with reference to FIGS. 1-6. In some embodiments, a computer program product is referred to as a non-transitory computer readable medium storing or comprising instructions to perform certain operations or functions. Examples of a computer program product include firmware, software driver, operating system, or software application. Examples of a software application include data management application (e.g., file management application, document management application, media management application, database application, etc.), communication application (e.g., email application, messaging application, teleconference or meeting application, social media application, etc.), productivity application (e.g., document viewer application, document creation or editing application, etc.), media or interactive application (e.g., web browser, image or photo viewer, audio or video playback application, gaming application, virtual or augmented reality application, shopping application, recommendation or review application, etc.), creativity application (e.g., image, drawing, photo, audio, or video creation or editing application, web page development application, virtual or augmented reality creation or editing application, graphic design application, etc.), or the like.

Communication interface 706 is used by computing device 700 to communicate with one or more communication networks, and/or other electronic device(s). Example types of communication networks include wired communication networks and/or wireless communication networks. Example types of communication networks include the Internet, a wide-area network, a local-area network, a virtual private network (VPN), an Intranet, or the like. In some embodiments, communication interface 706 utilizes various drivers, wireless communication circuitry, network interface circuitry, or the like to enable communication via various communication networks.

I/O interface 708 includes various drivers and/or hardware circuitry for receiving input from various input devices, providing output to various output devices, or exchanging input/output with various input/output devices. Examples of devices coupled to I/O interface 708 include peripheral devices such as a printer, a docking station, a communication hub, a charging device, etc. In some implementations, some devices coupled to I/O interface 708 are used as user interface component(s) 710. In one example, a user operates input elements of user interface component(s) 710 to invoke the functionality of computing device 700 and/or of another device communicatively coupled to computing device 700; a user views, hears, and/or otherwise experiences output from computing device 700 via output elements of user interface component(s) 710. Some user interface component(s) 710 provide both input and output functionalities. Examples of input user interface component include a mouse, a joystick, a keyboard, a microphone, a camera, or the like. Examples of output user interface component include a display screen (e.g., a monitor, an LCD display, etc.), one or more speakers, or the like. Examples of a user interface components provide both input and output functionalities include a touchscreen, haptic feedback controllers, or the like.

The foregoing description of the specific embodiments will so reveal the general nature of the present disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. It is intended that the specification and examples be considered as exemplary only, with a true scope being indicated by the following claims and their equivalents.

Embodiments of the present disclosure have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The Summary and Abstract sections may set forth one or more but not all exemplary embodiments of the present disclosure as contemplated by the inventor(s), and thus, are not intended to limit the present disclosure and the appended claims in any way.

Various functional blocks, modules, and steps are disclosed above. The particular arrangements provided are illustrative and without limitation. Accordingly, the functional blocks, modules, and steps may be re-ordered or combined in different ways than in the examples provided above. Likewise, certain embodiments include only a subset of the functional blocks, modules, and steps, and any such subset is permitted.

The breadth and scope of the present disclosure should not be limited by any of the above-described exemplary embodiments, but should be defined only in accordance with the following claims and their equivalents.

What is claimed is:

1. A Radio Detection and Ranging (Radar) system for detecting presence of a living thing, comprising:
a transmitter/receiver module configured to:
emit radio signals to an environment surrounding the Radar system; and
detect returned radio signals returned from the environment; and
a processing module configured to determine the presence of the living things based on the returned radio signals, comprising:
a large-movement detection sub-module configured to determine a large movement of the living thing based on the returned radio signals;
a micro-movement detection sub-module configured to determine a micro movement of the living thing based on the returned radio signals;
a breath and heartbeat detection sub-module configured to determine a breath or heartbeat of the living thing based on the returned radio signals; and
a presence detection sub-module configured to:
receive determinations from the large-movement detection sub-module, the micro-movement detection sub-module, and the breath and heartbeat detection sub-module respectively; and
determine the presence of the living thing based on aggregating the received determinations from the large-movement detection sub-module, the micro-movement detection sub-module, and the breath and heartbeat detection sub-module.

2. The Radar system of claim 1 further comprises a first pre-process sub-module, configured to pre-process the returned radio signals, wherein the first pre-process sub-module is configured to:
receive the returned radio signals from the transmitter and receiver module;
filter the returned radio signals using a first low-pass filter; and
generate a first pre-processed result by down sampling the returned radio signals using a first digital down-converter.

3. The Radar system of claim 2, wherein the large-movement detection sub-module is further configured to:
receive the first pre-processed result from the first pre-process sub-module;
filter the first pre-processed result using a band-stop filter to filter out noises within a certain frequency band;
filter out mutations in the first pre-processed result based on time-domain analysis of the first pre-processed result; and
determine the large movement of the living thing based on applying a first sliding window algorithm to the filtered first pre-processed result.

4. The Radar system of claim 3, wherein to perform the time-domain analysis, the large-movement detection sub-module is further configured to determine at least one of an amplitude or a value range of the filtered first pre-processed result.

5. The Radar system of claim 3, wherein to apply the first sliding window algorithm to determine the large movement of the living thing, the large-movement detection sub-module is further configured to:
divide the filtered first pre-processed result into multiple frames based on the first sliding window algorithm;
determine a value range of the filtered first pre-processed result in each frame of the filtered first pre-processed result; and
determine the large movement if the value range is higher than a first predetermined threshold.

6. The Radar system of claim 2, further comprises a second pre-process sub-module, configured to further pre-process the first pre-processed result received from the first pre-process sub-module, wherein the second pre-process module is configured to:
filter the first pre-processed result using a second low-pass filter; and
generate a second pre-processed result by down sampling the first pre-processed result using a second digital down-converter.

7. The Radar system of claim 6, wherein the micro-movement detection sub-module is further configured to:
filter the second pre-processed result, by a third low-pass filter to filter out noises below a certain frequency;
filter out mutations in the second pre-processed result based on a time-domain analysis of the second pre-processed result; and
determine the micro-movement of the living thing based on applying a second sliding window algorithm to the filtered second pre-processed result.

8. The Radar system of claim 7, wherein to perform the time-domain determinations, the micro-movement detection sub-module is further configured to determine at least one of an amplitude or a value range of the filtered second pre-processed result.

9. The Radar system of claim 7, wherein to apply the second sliding window algorithm to determine the micro-movement of the living thing, the micro-movement detection module is further configured to:
divide the filtered second pre-processed result into multiple frames based on the second sliding window algorithm;
determine a value range of the filtered second pre-processed result in each frame of the filtered second pre-processed result; and
determine the micro movement of the living thing if the value range is higher than a second predetermined threshold.

10. The Radar system of claim 6, wherein the breath and heartbeat detection sub-module is further configured to:
transform the second pre-processed result to frequency domain; and
determine if an energy level of the second pre-processed result within a pre-determined frequency range is higher than a third pre-determined level.

11. The Radar system of claim 6, wherein the breath and heartbeat detection sub-module is further configured to determine a breath frequency of the living thing based on a frequency of signals in the second pre-processed result within a pre-determined frequency range that has maximum energy level.

12. The Radar system of claim 1, wherein the presence detection sub-module is further configured to determine the presence of the living thing if at least one of the large movement, the micro movement, or the breath or heartbeat of the living thing is determined by the corresponding determination sub-module.

13. A method for detecting presence of a living thing implemented by a Radio Detection and Ranging (Radar) system, comprising:

emitting, by a transmitter/receiver module, radio signals to an environment surrounding the Radar system;
detecting, by the transmitter/receiver module, returned radio signals returned from the environment;
determining, by a large-movement detection sub-module, a large movement of the living thing based on the returned radio signals;
determining, by a micro-movement detection sub-module, a micro movement of the living thing based on the returned radio signals;
determining, by a breath and heartbeat detection sub-module, a breath or heartbeat of the living thing based on the returned radio signals; and
determining, by a presence detection sub-module, the presence of the living thing based on aggregating the determination of the large movement, the micro movement, and the breath or heartbeat of the living thing determined by the corresponding determination sub-module.

14. The method of claim 13, further comprises:
filtering the returned radio signals using a first low-pass filter; and
generating a first pre-processed result by down sampling the returned radio signals using a first digital down-converter.

15. The method of claim 14, further comprises:
filtering, by the large-movement detection sub-module, the first pre-processed result using a band-stop filter to filter out noises within a certain frequency band;
filtering out, by the large-movement detection sub-module, mutations in the first pre-processed result based on time-domain analysis of the pre-processed result; and
determining, by the large-movement detection sub-module, the large movement of the living thing based on applying a first sliding window algorithm to the filtered first pre-processed result.

16. The method of claim 14, further comprises:
filtering the first pre-processed result using a second low-pass filter; and
generating a second pre-processed result by down sampling the first pre-processed result using a first digital down-converter.

17. The method of claim 16, further comprises:
filtering, the micro-movement detection sub-module, the second pre-processed result using a third low-pass filter to filter out noises below a certain frequency;
filtering out, the micro-movement detection sub-module, mutations in the second pre-processed result based on time-domain analysis of the pre-processed returned radio signals; and
determining, the micro-movement detection sub-module, the micro movement of the living thing based on applying a second sliding window algorithm to the filtered second pre-processed result.

18. The method of claim 16, further comprises:
transforming, by the breath and heartbeat detection sub-module, the second pre-processed result to frequency domain; and
determining, by the breath and heartbeat detection sub-module, if an energy level of the second pre-processed result within a predetermined frequency range is higher than a predetermined level.

19. The method of claim 16, further comprises:
determining, by the breath and heartbeat detection sub-module, a breath frequency of the living thing based on a frequency of signals in the second pre-processed result within a predetermined frequency range that has a maximum energy level.

20. A non-transitory computer-readable medium encoded with instructions that, when executed by at least one processor of an apparatus, perform a process comprising:
emitting, by a transmitter/receiver module, radio signals to an environment surrounding a Radar system;
detecting, by the transmitter/receiver module, returned radio signals returned from the environment;
generating, by a first pre-process sub-module, a first pre-processed result by filtering the returned radio signals using a first low-pass filter and by down sampling the returned radio signals using a first digital down-converter;
determining, by a large-movement detection sub-module, a large movement of the living thing based on the first pre-processed result;
generating, by a second pre-process sub-module, a second pre-processed result by filtering first pre-processed result using a second low-pass filter and by down sampling the first pre-processed result using a second digital down-converter;
determining, by a micro-movement detection sub-module, a micro movement of the living thing based on the second pre-processed result;
transforming, by a breath and heartbeat detection sub-module, the second pre-processed result to frequency domain;
determining, by the breath and heartbeat detection sub-module, if an energy level of the second pre-processed result within a predetermined frequency range is higher than a predetermined level; and
determining, by a presence determination sub-module, the presence of a living thing based on aggregating the determination of the large movement, the micro movement, and the breath or heartbeat determined by the corresponding determination sub-module.

* * * * *